(12) United States Patent
Malyugin

(10) Patent No.: US 10,537,470 B2
(45) Date of Patent: *Jan. 21, 2020

(54) RING USED IN A SMALL PUPIL PHACOEMULSIFICATION PROCEDURE

(71) Applicant: Boris Malyugin, Moscow (RU)

(72) Inventor: Boris Malyugin, Moscow (RU)

(*) Notice: Subject to any disclaimer, the term of this patent is extended or adjusted under 35 U.S.C. 154(b) by 464 days.

This patent is subject to a terminal disclaimer.

(21) Appl. No.: 13/661,982

(22) Filed: Oct. 26, 2012

(65) Prior Publication Data

US 2013/0053860 A1  Feb. 28, 2013

Related U.S. Application Data

(63) Continuation of application No. 12/074,742, filed on Mar. 5, 2008, now Pat. No. 8,323,296.

(60) Provisional application No. 60/918,405, filed on Mar. 15, 2007.

(51) Int. Cl.
| | | |
|---|---|---|
| *A61B 17/02* | (2006.01) | |
| *A61F 9/007* | (2006.01) | |
| *A61F 9/00* | (2006.01) | |

(52) U.S. Cl.
CPC ...... *A61F 9/00736* (2013.01); *A61B 17/0231* (2013.01); *A61F 9/0017* (2013.01)

(58) Field of Classification Search
CPC .......... A61F 2/147; A61F 9/0008; A61F 2009/00887; A61F 9/00; A61F 9/007; A61F 9/00736; A61B 17/0231
See application file for complete search history.

(56) References Cited

U.S. PATENT DOCUMENTS

| | | |
|---|---|---|
| 1,506,186 A | 8/1924 | Owen et al. |
| 2,761,457 A | 9/1956 | Wood |
| 3,975,779 A | 8/1976 | Richards et al. |
| 4,203,168 A | 5/1980 | Rainin et al. |
| 4,321,916 A | 3/1982 | McKee |
| 4,387,706 A | 6/1983 | Glass |
| 4,412,532 A | 11/1983 | Anthony |
| 4,446,582 A | 5/1984 | Hanna |
| 4,782,820 A | 11/1988 | Woods |

(Continued)

FOREIGN PATENT DOCUMENTS

| | | |
|---|---|---|
| DE | 93 20 127 U1 | 4/1994 |
| RU | 14506 U1 | 2/2000 |

(Continued)

OTHER PUBLICATIONS

He et al, "Distribution and Heritability of Iris Thickness and Pupil Size in Chinese: The Guangzhou Twin Eye Study", Apr. 2009, IOVS ARVO Journal, vol. 50, Issue 4, pp. 1593-1597.*

(Continued)

*Primary Examiner* — Paul B Prebilic
(74) *Attorney, Agent, or Firm* — Hamilton, Brook, Smith & Reynolds, P.C.

(57) ABSTRACT

A ring that can maintain a pupil in an extended position during an ophthalmic procedure. The ring has a plurality of loops that capture iris tissue. The ring is configured to extend the pupil when iris tissue is inserted into each loop. An ophthalmic procedure such as phacoemulsification can then be performed on the patient. The ring has a center opening that provides a wide view of the ocular chamber during the procedure.

14 Claims, 4 Drawing Sheets

(56) References Cited

U.S. PATENT DOCUMENTS

| | | |
|---|---|---|
| 4,991,567 A | 2/1991 | McCuen et al. |
| 5,163,419 A | 11/1992 | Goldman |
| 5,267,553 A | 12/1993 | Graether |
| 5,299,564 A | 4/1994 | Sabatino |
| 5,318,011 A | 6/1994 | Federman et al. |
| 5,322,054 A | 6/1994 | Graether |
| 5,334,217 A | 8/1994 | Das |
| 5,374,272 A | 12/1994 | Arpa et al. |
| 5,441,045 A | 8/1995 | Federman |
| 5,456,274 A | 10/1995 | Selbee et al. |
| 5,489,295 A | 2/1996 | Piplani et al. |
| 5,634,884 A * | 6/1997 | Graether ............ A61B 17/0231 600/210 |
| 5,693,085 A | 12/1997 | Buirge et al. |
| 5,951,565 A | 9/1999 | Freeman |
| 6,068,643 A | 5/2000 | Milverton |
| 6,200,336 B1 | 3/2001 | Pavcnik et al. |
| 6,231,583 B1 | 5/2001 | Lee |
| 6,332,866 B1 * | 12/2001 | Grieshaber ........ A61B 17/0231 600/210 |
| 6,497,724 B1 | 12/2002 | Stevens et al. |
| 6,620,098 B1 | 9/2003 | Milverton |
| 6,814,748 B1 | 11/2004 | Baker et al. |
| 7,305,996 B2 | 12/2007 | Kraft et al. |
| 7,412,993 B2 | 8/2008 | Tzeng |
| 7,985,180 B2 | 7/2011 | Brown |
| 8,257,256 B1 | 9/2012 | Krolman |
| 8,323,296 B2 | 12/2012 | Malyugin |
| 8,376,743 B1 | 2/2013 | Bukhary |
| 8,496,583 B1 | 7/2013 | Reynard |
| 8,900,136 B2 | 12/2014 | Cote et al. |
| 9,089,397 B2 | 7/2015 | Clarke |
| 9,504,459 B1 | 11/2016 | Nallakrishnan |
| 9,763,653 B2 | 9/2017 | Malyugin |
| 9,918,710 B2 | 3/2018 | Malyugin et al. |
| 10,080,558 B2 * | 9/2018 | Bhattacharjee .... A61B 17/0293 |
| 2003/0092970 A1 | 5/2003 | Lee |
| 2008/0108879 A1 | 5/2008 | Brown |
| 2008/0243139 A1 | 10/2008 | Dusek |
| 2008/0269888 A1 | 10/2008 | Malyugin |
| 2008/0275461 A1 | 11/2008 | Nallakrishnan |
| 2012/0136322 A1 | 5/2012 | Alster et al. |
| 2012/0289786 A1 | 11/2012 | Dusek |
| 2013/0096386 A1 | 4/2013 | Christensen et al. |
| 2013/0131458 A1 | 5/2013 | Malugin et al. |
| 2013/0267988 A1 | 10/2013 | Sussman et al. |
| 2013/0331939 A1 | 12/2013 | Stevens |
| 2014/0221759 A1 | 8/2014 | Mackool et al. |
| 2014/0378773 A1 | 12/2014 | Dykes |
| 2015/0164685 A1 | 6/2015 | Bhattacharjee |
| 2015/0265269 A1 * | 9/2015 | Malyugin ................ A61B 1/32 600/236 |

FOREIGN PATENT DOCUMENTS

| | | |
|---|---|---|
| RU | 14505 U1 | 9/2000 |
| WO | WO 95/15120 | 6/1995 |
| WO | WO 00/32141 | 6/2000 |
| WO | WO 2008/115455 A1 | 9/2008 |

OTHER PUBLICATIONS

Office Action dated May 9, 2013 in U.S. Appl. No. 13/466,968, "Expansion Ring for Eyeball Tissue."

Supplementary European Search Report dated May 23, 2011 for International Application No. PCT/US08/03472.

International Search Report dated Jul. 23, 2008 for International Application No. PCT/US08/03472.

International Preliminary Report on Patentability dated Sep. 15, 2009 for International Application No. PCT/US08/03472.

Cimberle, M., "New Pupil Expander Easier to Implant, Gentle on the Iris," *Ocular Surgery News Europe Asia Edition*, [online], May 2006 [retrieved on Mar. 27, 2013]. Retrieved from the Internet URL: http://www.osnsupersite.com/view.aspx?rid=16863.

Office Action dated Aug. 25, 2014 in U.S. Appl. No. 13/466,968, entitled "Expansion Ring for Eyeball Tissue".

Office Communication, U.S. Appl. No. 13/466,968, filed May 8, 2012, entitled "Expansion Ring for Eyeball Tissue", Date of Communication: Jun. 30, 2015.

Office Communication, U.S. Appl. No. 14/732,262, filed Jun. 5, 2015, entitled "Expansion Ring for Eyeball Tissue", Date of Communication: Jun. 30, 2015.

Office Communication, U.S. Appl. No. 14/732,262, filed Jun. 5, 2015, Date of Communication: Mar. 10, 2016.

Office Communication, U.S. Appl. No. 13/466,968, filed May 8, 2012, Date of Communication: Mar. 11, 2016.

Final Office Action for U.S. Appl. No. 13/466,968, entitled "Expansion Ring for Eyeball Tissue", dated Dec. 12, 2014.

Notice of Allowance for U.S. Appl. No. 14/732,262, entitled "Expansion Ring for Eyeball Tissue", dated May 24, 2017.

\* cited by examiner

RING USED IN A SMALL PUPIL PHACOEMULSIFICATION PROCEDURE

RELATED APPLICATIONS

This application is a continuation of U.S. application Ser. No. 12/074,742, filed Mar. 5, 2008, now U.S. Pat. No. 8,323,296 which claims the benefit of U.S. Provisional Application No. 60/918,405 filed on Mar. 15, 2007.

The entire teachings of U.S. application Ser. No. 12/074,742 are incorporated herein by reference.

BACKGROUND OF THE INVENTION

Field of the Invention

The present invention relates to a ring used in a ophthalmic surgical procedure.

Background Information

There are various ophthalmic procedures that require the dilation of the pupil. For example, cataracteous lenses are typically replaced in a procedure commonly referred to as phacoemulsification or phaco for short. In a phaco procedure the lens is broken up with an instrument, typically with an ultrasonically driven tool. The instrument has an aspiration port that aspirates the broken lens material from the patient's ocular chamber.

It is desirable to extend the pupil during a phaco procedure to provide the surgeon with a wide view of the lens. One technique for extending the pupil includes pulling back the iris with a series of plastic hooks. It is has been found that using plastic hooks can cause damage to iris tissue.

SUMMARY OF THE INVENTION

A ring used to maintain a pupil in an extended position during an ophthalmic procedure. The ring has a plurality of loops.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Described is a ring that can maintain a pupil in an extended position during an ophthalmic procedure. The ring has a plurality of loops that capture iris tissue. The ring is configured to extend the pupil when iris tissue is inserted into each loop. An ophthalmic procedure such as phacoemulsification can then be performed on the patient. The ring has a center opening that provides a wide view of the ocular chamber during the procedure.

Figure 1:
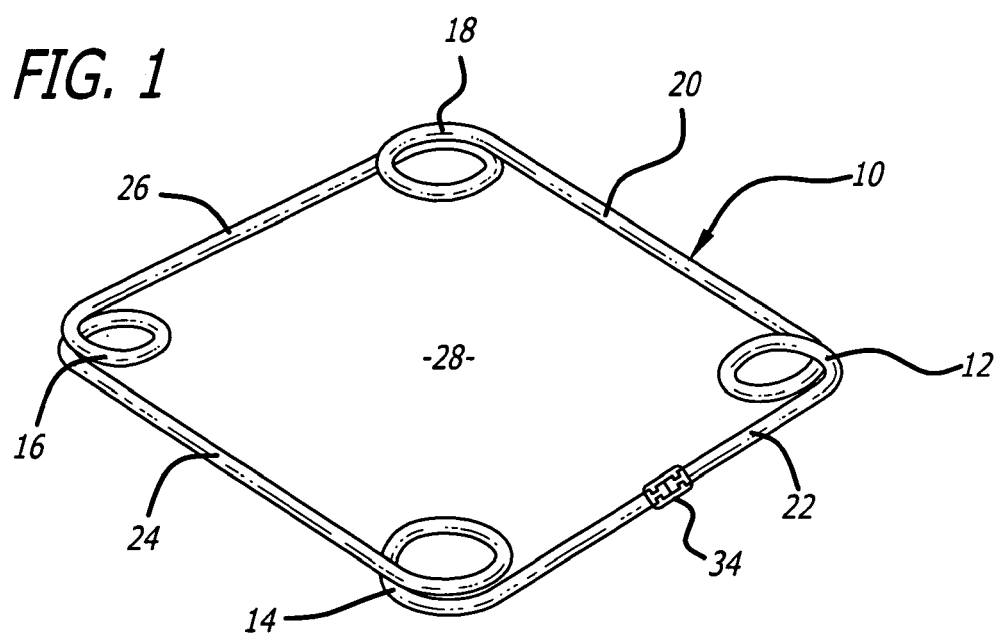
FIG. 1 is an illustration of a ring of the present invention.

Referring to the drawings more particularly by reference numbers, FIG. 1 shows an embodiment of a ring 10 that can be used to extend a .pupil during an ophthalmic procedure. The ring 10 has a plurality of loops 12, 14, 16 and 18 located at the corners of four sides 20, 22, 24 and 26. Each loop 12, 14, 16 and 18 may be formed by one full turn. Although one full turn is shown and described, it is to be understood that each loop 12, 14, 16 and 18 may have multiple turns. The four sides 20, 22, 24 and 26 circumscribe a center opening 28.

The ring 10 preferably has a square configuration such that the sides 20, 22, 24 and 26 are of equal dimension. Although a square ring is shown and described, it is to be understood that the ring may have a rectangular configuration where all sides 20, 22, 24 and 26 are not of equal dimension. Addi~ionally, the ring may have a nonrectangular shape. For example, the ring 10 may be shaped as a triangle that has three sides and three loops located at the ring corners. Although three and four sided rings have been described, it is to be understood that the ring may have any number of side and loops. The ring 10 is preferably constructed from a molded plastic material, although it is to be understood that other materials such as metal or plastic coated metal may be employed.

Figure 2:
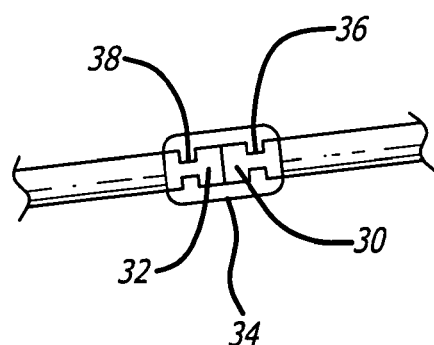
FIG. 2 is an illustration showing an enlarged view of the ring.

FIG. 2 shows a preferred embodiment for constructing the ring 10. One side 20 of the ring 10 has two ends 30 and 32 that are butt attached by an adhesive 34. Each end 30 and 32 may have an indent 36 and 38, respectively. The adhesive 34 can flow into the indents 36 and 38 to increase the strength of the butt attachment of the ring 10. The indents 36 and 38 create surface structure that minimizes shearing and delamination of the adhesive 34 from the ring 10. By way of example, the adhesive 34 may be a biocompatible material such as Class VI epoxy. The adhesive 34 can be applied with a tool (not shown) that insures a repeatable volume and dimensions of the solidified adhesive form.

Figure 3:
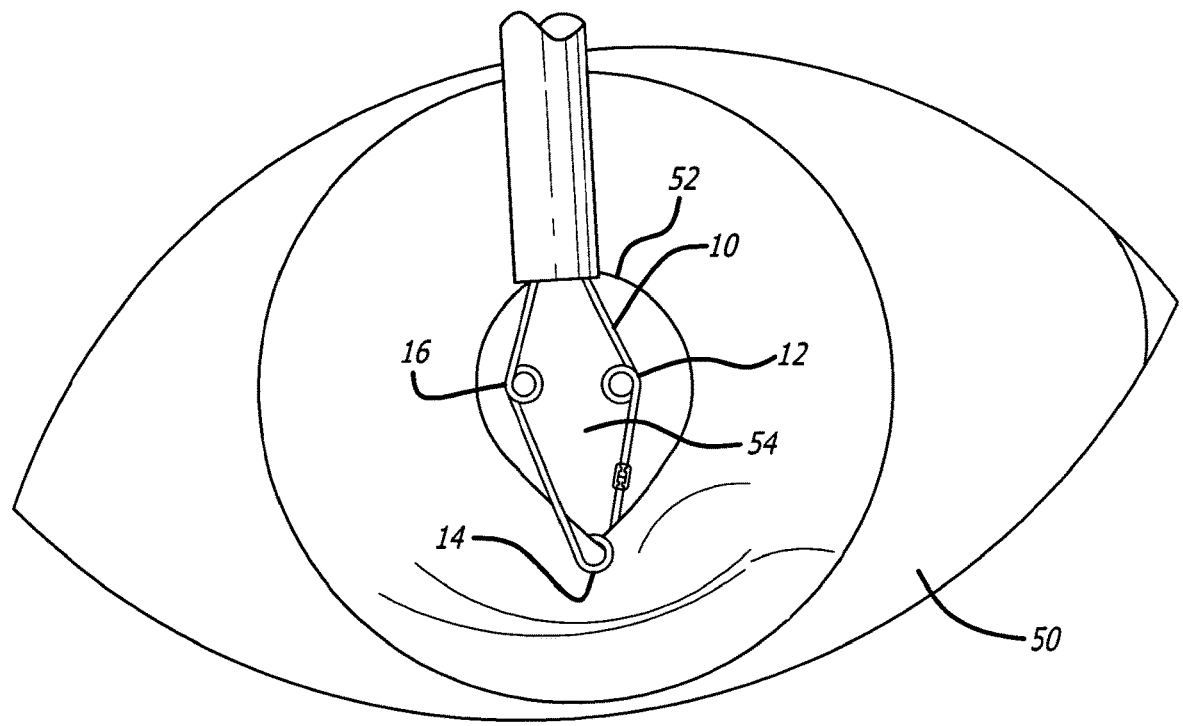
FIG. 3 is an illustration showing iris tissue being inserted into a first loop of the ring.
Figure 4:
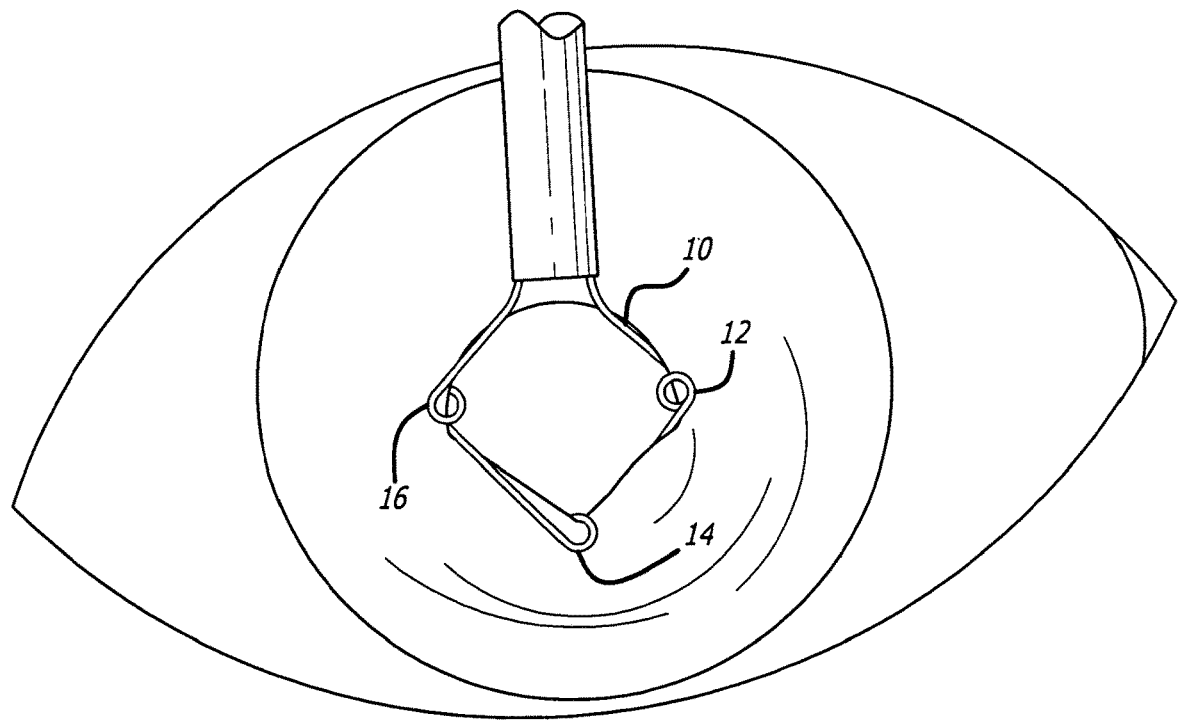
FIG. 4 is an illustration showing iris tissue being inserted into a second loop of the ring.

FIG. 3 shows the initial stages of the ring 10 being inserted into a patient's eye 50 to stretch the iris 52 and extend the pupil 54. A tool such as a forceps (not shown) can be used to pull the iris so that iris tissue is inserted into loop 14 of the ring 10. As shown in FIG. 4, the ring 10 can be manipulated so that iris tissue is inserted into loops 12 and 16.

Figure 5:
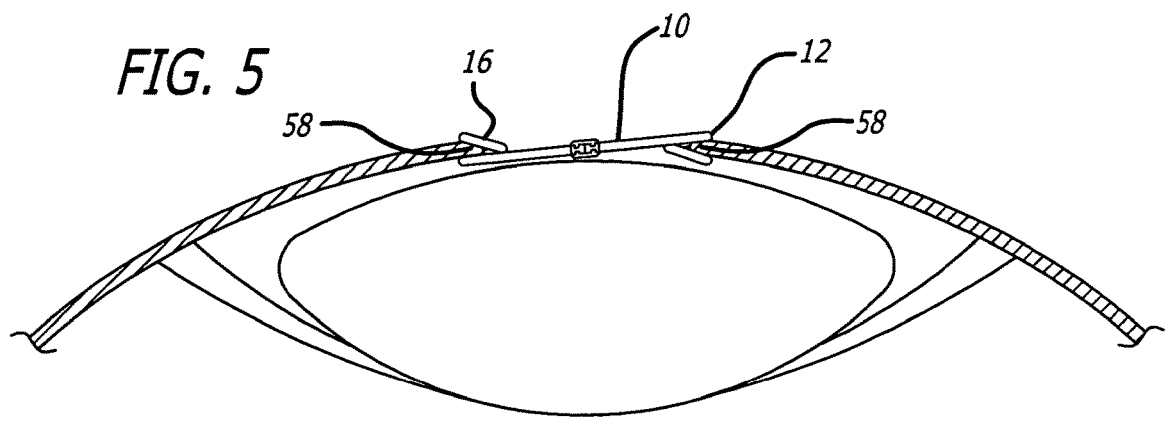
FIG. 5 is an illustration showing the iris tissue within gaps of the loops.

As shown in FIG. 1, an example of the device of the present invention is a polygonal ring formed from a single strand. As shown in FIG. 5 each loop 12, 16, etc. has a gap 58 that receives and captures iris tissue. The gap is wedge-shaped and faces the periphery of the ring 10. It is formed between a top portion of the strand and a bottom portion of the strand. The loop design provides an easy means of inserting and capturing iris tissue. The flexibility of the ring 10 allows the loops to deflect and apply a clamping force onto the iris tissue. The clamping force assist in maintaining the position of the ring relative to the eye.

Figure 6:
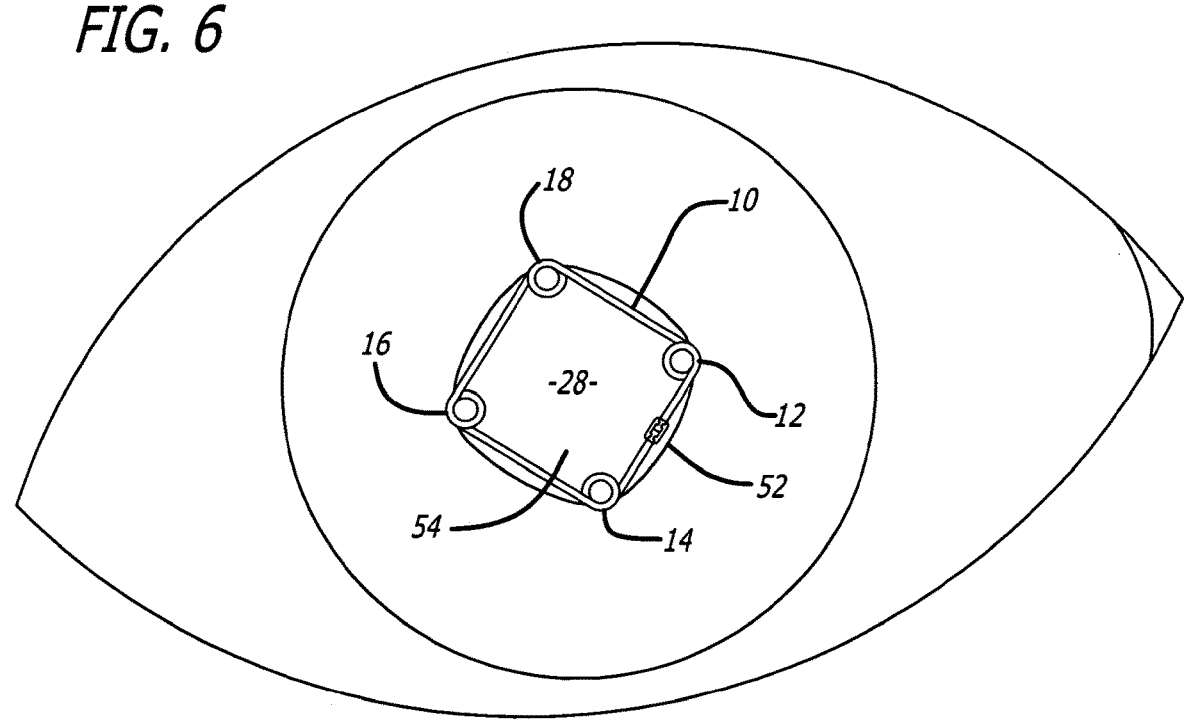
FIG. 6 is an illustration showing a pupil being maintained in an extended position by the ring.

As shown in FIG. 6 iris tissue can be inserted into the second 14 and fourth 18 loops to fully stretch the iris 52 and extend the pupil 54. An ophthalmic procedure can then be performed on the eye. For example, a phaco procedure can be performed wherein the lens is emulsified and aspirated from the eye. The ring 10 maintains the pupil' 54 in the fully extended position while the center opening 28 provides a wide viewing area during the procedure. When the procedure is complete one of the sides 20, 22, 24 or 26 can be cut with an instrument and the ring 10 can be removed from the eye.

Figure 7:
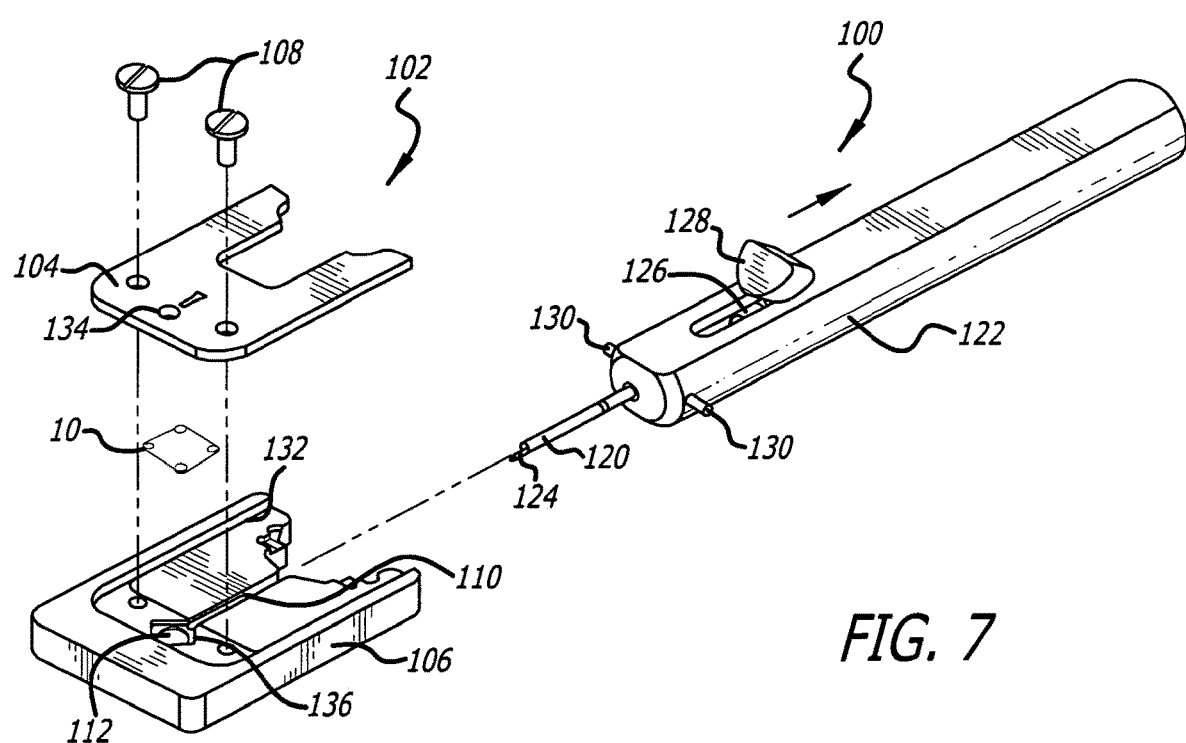
FIG. 7 is a perspective view of an injector and ring plate used to load and inject the ring.

FIG. 7 shows an embodiment of an injector 100 that can be used to inject a ring 10 into a patient's eye. The ring 10 can be loaded into the injector with the use of a ring plate 102. The ring plate 102 may include a cover 104 that is attached to a base plate 106 by fasteners 108. The base plate 106 has a channel 110 and a recess 112. The recess 112 receives the ring 10.

The injector 100 includes a cannula 120 attached to a handle 122. Within the cannula 120 is a wire hook 124. The wire hook 124 is connected to an inner slide tube 126 located within the handle 122. A button 128 is attached to the inner slide tube 126. The injector 100 may also have a pair of guide pins 130 that are attached to the handle 122 and cooperate with corresponding channel features 132 of the base plate 106 to properly align the injector 100 when the cannula 120 is inserted into the base plate channel 110.

In operation, the cannula 120 is inserted into the base plate channel 110. When fully inserted the wire hook 124 extends to approximately the center of the ring 10. The cover 104 may have an opening 134 that allows an operator to visually see the hook 124 within the ring opening. An operator then pulls the button 128 in the direction indicated by the arrow. Pulling the button 128 causes the hook 124 to grasp the ring loops and pull the ring 10 into the cannula 120. The recess 112 has tapered walls 136 to assist in the ring collapsing within the channel 112 for insertion into the cannula 120. Once loaded, the ring 10 can be injected into a patient's eye by pushing the button 128 in the opposite direction.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An ophthalmic ring sized to maintain a pupil of a subject's eye in an extended position during an ophthalmic procedure, the ring comprising:
    a strand, the strand including:
        at least three side elements; and
        at least three loops, each loop further including a top portion and a bottom portion,
    wherein, in the extended ring position:
        each side element of the at least three side elements connects the top portion and the bottom portion of two adjacent loops of the at least three loops to form the ring, the ring circumscribing a central opening through which a posterior chamber of the subject's eye can be accessed during the ophthalmic procedure, the central opening being disposed in a plane between the at least three side elements and the at least three loops, and
        each loop of the at least three loops defines an iris-retaining gap between the top portion and the bottom portion of the loop, the iris-retaining gap of each loop facing away from the central opening of the ring and dimensioned to receive iris tissue of the subject's eye during the ophthalmic procedure.

2. The ring of claim 1, wherein the top portion and the bottom portion of each loop are disposed at an angle with respect to one another.

3. The ring of claim 1, wherein each loop makes at least one full turn.

4. The ring of claim 1, wherein each loop makes more than one full turn.

5. The ring of claim 1, wherein the ring includes four loops.

6. The ring of claim 5, wherein the ring is a square.

7. The ring of claim 1, wherein the ring is configured to adapt one or more of configurations selected from a folded configuration or an extended configuration.

8. The ring of claim 1, wherein the strand includes a first end and a second end, the first and second ends being attached to each other.

9. The ring of claim 1, wherein the loops are disposed equidistantly along the ring.

10. The ring of claim 1, wherein each loop is disposed in the plane of the central opening.

11. The ring of claim 1, wherein at least one of the side elements is configured to maintain a constant length during an ophthalmic procedure and after each of the loops receives iris tissue.

12. The ring of claim 1, wherein the ring is configured to transition between a collapsed position prior to insertion into the subject's eye and an extended position when the ring is fully inserted, and wherein a length of each of the at least three side elements is constant in both the collapsed and extended positions.

13. The ring of claim 12, wherein the loops are configured to apply an outward bias on iris tissue when the ring is inserted into the subject's eye.

14. The ring of claim 1, wherein each side element connects one top portion and one bottom portion of two adjacent loops.

* * * * *